(12) United States Patent
Arbelbide et al.

(10) Patent No.: US 11,700,821 B1
(45) Date of Patent: Jul. 18, 2023

(54) MAIZE HYBRID X95R013

(71) Applicant: PIONEER HI-BRED INTERNATIONAL, INC., Johnston, IA (US)

(72) Inventors: Martin Arbelbide, Eau Claire, WI (US); Martin A Fabrizius, Willmar, MN (US); Christopher Michael Schaefer, Volga, SD (US); Matthew David Walch, Moorhead, MN (US)

(73) Assignee: PIONEER HI-BRED INTERNATIONAL, INC.

( * ) Notice: Subject to any disclaimer, the term of this patent is extended or adjusted under 35 U.S.C. 154(b) by 98 days.

(21) Appl. No.: 17/377,443

(22) Filed: Jul. 16, 2021

(51) Int. Cl.
  *A01H 6/46* (2018.01)
  *A01H 5/10* (2018.01)

(52) U.S. Cl.
  CPC ............ *A01H 6/4684* (2018.05); *A01H 5/10* (2013.01)

(58) Field of Classification Search
  None
  See application file for complete search history.

(56) References Cited

U.S. PATENT DOCUMENTS 9,894,867 B1 * 2/2018 Chandler ............. A01H 6/4684

OTHER PUBLICATIONS

Fehr (Principles of Cultivar Development, vol. 1: Theory and technique, pp. 360-376, 1987). (Year: 1987).*
U.S. Appl. No. 17/366,094 for Maize Inbred 1PCWH37, filed Jul. 2, 2021.
U.S. Appl. No. 17/366,167 for Maize Inbred PH4D4R, filed Jul. 2, 2021.

* cited by examiner

*Primary Examiner* — Charles Logsdon

(57) ABSTRACT

A novel maize variety designated X95R013 and seed, plants and plant parts thereof are produced by crossing inbred maize varieties. Methods for producing a maize plant by crossing hybrid maize variety X95R013 with another maize plant are disclosed. Methods for producing a maize plant containing in its genetic material one or more traits introgressed into X95R013 through backcrossing or genetic transformation, and to the maize seed, plant and plant part produced thereby are described. Maize variety X95R013, the seed, the plant produced from the seed, and variants, mutants, and minor modifications of maize variety X95R013 are provided. Methods for producing maize varieties derived from maize variety X95R013 and methods of using maize variety X95R013 are disclosed.

20 Claims, No Drawings

MAIZE HYBRID X95R013

BACKGROUND

The goal of hybrid development is to combine, in a single hybrid, various desirable traits. For field crops, these traits may include resistance to diseases and insects, resistance to heat and drought, reducing the time to crop maturity, greater yield, and better agronomic quality. With mechanical harvesting of many crops, uniformity of plant characteristics such as germination, stand establishment, growth rate, maturity, and plant and ear height is important. Traditional plant breeding is an important tool in developing new and improved commercial crops.

SUMMARY

Provided is a novel maize, Zea mays L., variety, seed, plant, cells and its parts designated as X95R013, produced by crossing two maize inbred varieties. The hybrid maize variety X95R013, the seed, the plant and its parts produced from the seed, and variants, mutants and minor modifications of maize X95R013 are provided. Processes are provided for making a maize plant containing in its genetic material one or more traits introgressed into X95R013 through locus conversion, backcrossing and/or transformation, and to the maize seed, plant and plant parts produced thereby. Methods for producing maize varieties derived from hybrid maize variety X95R013 are also provided. Also provided are maize plants having all the physiological and morphological characteristics of the hybrid maize variety X95R013.

The hybrid maize plant may further comprise a cytoplasmic or nuclear factor capable of conferring male sterility or otherwise preventing self-pollination, such as by self-incompatibility. Parts of the maize plants disclosed herein are also provided, for example, pollen obtained from a hybrid plant and an ovule of the hybrid plant. Seed of the hybrid maize variety X95R013 is provided and may be provided as a population of maize seed of the variety designated X95R013.

Compositions are provided comprising a seed of maize variety X95R013 comprised in plant seed growth media. In certain embodiments, the plant seed growth media is a soil or synthetic cultivation medium. In specific embodiments, the growth medium may be comprised in a container or may, for example, be soil in a field.

Hybrid maize variety X95R013 is provided comprising an added heritable trait. The heritable trait may be a genetic locus that is a dominant or recessive allele. In certain embodiments, the genetic locus confers traits such as, for example, male sterility, waxy starch, reduced lignin, herbicide tolerance or resistance, insect resistance, resistance to bacterial, fungal, nematode or viral disease, and altered or modified fatty acid, phytate, protein or carbohydrate metabolism. The genetic locus may be a naturally occurring maize gene introduced into the genome of a parent of the variety by backcrossing, a natural or induced mutation, or a transgene introduced through genetic transformation techniques. When introduced through transformation, a genetic locus may comprise one or more transgenes integrated at a single chromosomal location.

A hybrid maize plant of the variety designated X95R013 is provided, wherein a cytoplasmically-inherited trait has been introduced into the hybrid plant. Such cytoplasmically-inherited traits are passed to progeny through the female parent in a particular cross. An exemplary cytoplasmically-inherited trait is the male sterility trait. Cytoplasmic-male sterility (CMS) is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and continues to be male sterile in the next generation. The male fertility of a CMS plant can be restored by a restorer version of the same variety, which must have the restorer gene(s) in the nucleus. With the restorer gene(s) in the nucleus, the offspring of the male-sterile plant can produce normal pollen grains and propagate. A cytoplasmically inherited trait may be a naturally occurring maize trait or a trait introduced through genetic transformation techniques.

A tissue culture of regenerable cells of a plant of variety X95R013 is provided. The tissue culture can be capable of regenerating plants capable of expressing all of the physiological and morphological or phenotypic characteristics of the variety and of regenerating plants having substantially the same genotype as other plants of the variety. Examples of some of the physiological and morphological characteristics of the variety X95R013 that may be assessed include characteristics related to yield, maturity, and kernel quality. The regenerable cells in such tissue cultures can be derived, for example, from embryos, meristematic cells, immature tassels, microspores, pollen, leaves, anthers, roots, root tips, silk, flowers, kernels, ears, cobs, husks, or stalks, or from callus or protoplasts derived from those tissues. Maize plants regenerated from the tissue cultures and plants having all or essentially all of the physiological and morphological characteristics of variety X95R013 are also provided.

A method of producing hybrid maize seed comprising crossing a plant of variety 1PCWH37 with a plant of variety PH4D4R. In a cross, either parent may serve as the male or female. Processes are also provided for producing maize seeds or plants, which processes generally comprise crossing a first parent maize plant as a male or female parent with a second parent maize plant, wherein at least one of the first or second parent maize plants is a plant of the variety designated X95R013. In such crossing, either parent may serve as the male or female parent. These processes may be further exemplified as processes for preparing hybrid maize seed or plants, wherein a first hybrid maize plant is crossed with a second maize plant of a different, distinct variety to provide a hybrid that has, as one of its parents, the hybrid maize plant variety X95R013. In these processes, crossing will result in the production of seed. The seed production occurs regardless of whether the seed is collected or not.

In some embodiments, the first step in "crossing" comprises planting, often in pollinating proximity, seeds of a first and second parent maize plant, and in many cases, seeds of a first maize plant and a second, distinct maize plant. Where the plants are not in pollinating proximity, pollination can nevertheless be accomplished by other means, such as by transferring a pollen or tassel bag from one plant to the other.

A second step comprises cultivating or growing the seeds of said first and second parent maize plants into plants that bear flowers (maize bears both male flowers (tassels) and female flowers (silks) in separate anatomical structures on the same plant).

A third step comprises preventing self-pollination of the plants, i.e., preventing the silks of a plant from being fertilized by any plant of the same variety, including the same plant. This can be done, for example, by emasculating the male flowers of the first or second parent maize plant, (i.e., treating or manipulating the flowers so as to prevent pollen production, in order to produce an emasculated parent maize plant). Self-incompatibility systems may also be used in some hybrid crops for the same purpose. Self-incompatible plants still shed viable pollen and can pollinate plants of other varieties but are incapable of pollinating themselves or other plants of the same variety.

A fourth step may comprise allowing cross-pollination to occur between the first and second parent maize plants. When the plants are not in pollinating proximity, this can be done by placing a bag, usually paper or glassine, over the tassels of the first plant and another bag over the silks of the incipient ear on the second plant. The bags are left in place for at least 24 hours. Since pollen is viable for less than 24 hours, this assures that the silks are not pollinated from other pollen sources, that any stray pollen on the tassels of the first plant is dead, and that the only pollen transferred comes from the first plant. The pollen bag over the tassel of the first plant is then shaken vigorously to enhance release of pollen from the tassels, and the shoot bag is removed from the silks of the incipient ear on the second plant. Finally, the pollen bag is removed from the tassel of the first plant and is placed over the silks of the incipient ear of the second plant, shaken again and left in place. Yet another step comprises harvesting the seeds from at least one of the parent maize plants. The harvested seed can be grown to produce a maize plant or hybrid maize plant.

Maize seed and plants are provided that are produced by a process that comprises crossing a first parent maize plant with a second parent maize plant, wherein at least one of the first or second parent maize plants is a plant of the variety designated X95R013. Maize seed and plants produced by the process are first generation hybrid maize seed and plants produced by crossing an inbred with another, distinct inbred. Seed of an F1 hybrid maize plant, an F1 hybrid maize plant and seed thereof, specifically the hybrid variety designated X95R013 is provided.

Plants described herein can be analyzed by their "genetic complement." This term is used to refer to the aggregate of nucleotide sequences, the expression of which defines the phenotype of, for example, a maize plant, or a cell or tissue of that plant. A genetic complement thus represents the genetic makeup of a cell, tissue or plant. Provided are maize plant cells that have a genetic complement in accordance with the maize plant cells disclosed herein, and plants, seeds and diploid plants containing such cells.

Plant genetic complements may be assessed by genetic marker profiles, and by the expression of phenotypic traits that are characteristic of the expression of the genetic complement, e.g., isozyme typing profiles. It is understood that variety X95R013 could be identified by any of the many well-known techniques used for genetic profiling disclosed herein.

DETAILED DESCRIPTION

A new and distinctive maize hybrid variety designated X95R013, which has been the result of years of careful breeding and selection in a comprehensive maize breeding program is provided.

Definitions

Maize, *Zea mays* L., can be referred to as maize or corn. Certain definitions used in the specification are provided below. Also in the examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. PCT designates that the trait is calculated as a percentage. % NOT designates the percentage of plants that did not exhibit a trait. For example, STKLDG % NOT is the percentage of plants in a plot that were not stalk lodged. These designators will follow the descriptors to denote how the values are to be interpreted. Below are the descriptors used in the data tables included herein.

BRITTLE STALK: A count of the number of "snapped" plants per plot following machine snapping or artificial selection pressure. A snapped plant has its stalk completely snapped at a node between the base of the plant and the node above the ear. Can be expressed as percent of plants that did not snap.

ALLELE: Any of one or more alternative forms of a genetic sequence. In a diploid cell or organism, the two alleles of a given sequence typically occupy corresponding loci on a pair of homologous chromosomes.

ALTER: With respect to genetic manipulation, the utilization of up-regulation, down-regulation, or gene silencing.

ANTHESIS: The time of a flower's opening.

ANTHRACNOSE STALK ROT (*Colletotrichum graminicola*): A 1 to 9 visual rating indicating the resistance to Anthracnose Stalk Rot. A higher score indicates a higher resistance. Data are collected only when sufficient selection pressure exists in the experiment measured.

BLUP=BEST LINEAR UNBIASED PREDICTION. The BLUP values are determined from a mixed model analysis of hybrid performance observations at various locations and replications. BLUP values for inbred maize plants, breeding values, are estimated from the same analysis using pedigree information.

BREEDING CROSS: A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new inbred variety is developed.

CELL: Cell as used herein includes a plant cell, whether isolated, in tissue culture or incorporated in a plant or plant part.

CORN LETHAL NECROSIS: Synergistic interaction of maize chlorotic mottle virus (MCMV) in combination with either maize dwarf mosaic virus (MDMV-A or MDMV-B) or wheat streak mosaic virus (WSMV). A 1 to 9 visual rating indicating the resistance to Corn Lethal Necrosis. A higher score indicates a higher resistance. Data are collected only when sufficient selection pressure exists in the experiment measured.

COMMON SMUT: This is the percentage of plants not infected with Common Smut. Data are collected only when sufficient selection pressure exists in the experiment measured.

COMMON RUST (*Puccinia sorghi*): A 1 to 9 visual rating indicating the resistance to Common Rust. A higher score indicates a higher resistance. Data are collected only when sufficient selection pressure exists in the experiment measured.

CROSS POLLINATION: Fertilization by the union of two gametes from different plants.

CROSSING: The combination of genetic material by traditional methods such as a breeding cross or backcross, but also including protoplast fusion and other molecular biology methods of combining genetic material from two sources.

D and D1-Dn: represents the generation of doubled haploid.

DRYDOWN: This represents the relative rate at which a hybrid will reach acceptable harvest moisture compared to other hybrids on a 1 to 9 rating scale. A high score indicates a hybrid that dries relatively fast while a low score indicates a hybrid that dries slowly.

DIGESTIBLE ENERGY: Near-infrared transmission spectroscopy, NIT, prediction of digestible energy.

DIPLODIA EAR MOLD SCORES (*Diplodia maydis* and *Diplodia macrospora*): A 1 to 9 visual rating indicating the resistance to *Diplodia* Ear Mold. A higher score indicates a higher resistance. Data are collected only when sufficient selection pressure exists in the experiment measured DIPLODIA STALK ROT: Stalk rot severity due to *Diplodia* (*Diplodia maydis*). Expressed as a 1 to 9 score with 9 being highly resistant. Data are collected only when sufficient selection pressure exists in the experiment measured.

DROPPED EARS: A measure of the number of dropped ears per plot and represents the percentage of plants that did not drop ears prior to harvest. Data are collected only when sufficient selection pressure exists in the experiment measured.

DROUGHT TOLERANCE: This represents a 1 to 9 rating for drought tolerance, and is based on data obtained under stress conditions. A high score indicates good drought tolerance and a low score indicates poor drought tolerance. Data are collected only when sufficient selection pressure exists in the experiment measured.

EAR POSITION AT MATURITY: The position of the ear at physiological maturity (approximately 65 days after 50% silk) 1=Upright; 2=Horizontal; 3=Pendent.

EYE SPOT (*Kabatiella zeae* or *Aureobasidium zeae*): A 1 to 9 visual rating indicating the resistance to Eye Spot. A higher score indicates a higher resistance. Data are collected only when sufficient selection pressure exists in the experiment measured.

F1 PROGENY: A progeny plant produced by crossing a plant of one maize line with a plant of another maize line.

FUSARIUM EAR ROT (*Fusarium moniliforme* or *Fusarium subglutinans*): A 1 to 9 visual rating indicating the resistance to *Fusarium* Ear Rot. A higher score indicates a higher resistance. Data are collected only when sufficient selection pressure exists in the experiment measured.

GDU=GROWING DEGREE UNITS: Using the Barger Heat Unit Theory, which assumes that maize growth occurs in the temperature range 50° F.— 86° F. and that temperatures outside this range slow down growth; the maximum daily heat unit accumulation is 36 and the minimum daily heat unit accumulation is 0. The seasonal accumulation of GDU is a major factor in determining maturity zones.

GDUSHD=GDU TO SHED: The number of growing degree units (GDUs) or heat units required for an inbred variety or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The units determined by the Barger Method are then divided by 10. The highest maximum temperature used is 86 degrees F. and the lowest minimum temperature used is 50 degrees F. For each inbred or hybrid it takes a certain number of GDUs to reach various stages of plant development.

GDUSLK=GDU TO SILK: The number of growing degree units required for an inbred variety or hybrid to have approximately 50 percent of the plants with silk emergence from time of planting. Growing degree units are calculated by the Barger Method as given in GDUSHD definition and then divided by 10.

GENE SILENCING: The interruption or suppression of the expression of a gene at the level of transcription or translation.

GENOTYPE: Refers to the genetic mark-up or profile of a cell or organism.

GIBERS=*GIBBERELLA* EAR ROT (PINK MOLD) (*Gibberella zeae*): A 1 to 9 visual rating indicating the resistance to *Gibberella* Ear Rot. A higher score indicates a higher resistance. Data are collected only when sufficient selection pressure exists in the experiment measured.

GIBROT=*GIBBERELLA* STALK ROT SCORE: Score of stalk rot severity due to *Gibberella* (*Gibberella zeae*). Expressed as a 1 to 9 score with 9 being highly resistant. Data are collected only when sufficient selection pressure exists in the experiment measured.

GLFSPT=GRAY LEAF SPOT (*Cercospora zeae-maydis*): A 1 to 9 visual rating indicating the resistance to Gray Leaf Spot. A higher score indicates a higher resistance. Data are collected only when sufficient selection pressure exists in the experiment measured.

GOSWLT=GOSS' WILT (*Corynebacterium nebraskense*): A 1 to 9 visual rating indicating the resistance to Goss' Wilt. A higher score indicates a higher resistance. Data are collected only when sufficient selection pressure exists in the experiment measured.

GRAIN TEXTURE: A visual rating used to indicate the appearance of mature grain observed in the middle third of the uppermost ear when well developed. Grain or seed with a hard grain texture is indicated as flint; grain or seed with a soft grain texture is indicted as dent. Medium grain or seed texture may be indicated as flint-dent or intermediate. Other grain textures include flint-like, dent-like, sweet, pop, waxy and flour.

GRNAPP=GRAIN APPEARANCE: This is a 1 to 9 rating for the general appearance of the shelled grain as it is harvested based on such factors as the color of harvested grain, any mold on the grain, and any cracked grain. Higher scores indicate better grain visual quality.

H and H1: Refers to the haploid generation.

HAPLOID PLANT PART: Refers to a plant part or cell that has a haploid genotype.

HCBLT=*HELMINTHOSPORIUM CARBONUM* LEAF BLIGHT (*Helminthosporium carbonum*): A 1 to 9 visual rating indicating the resistance to *Helminthosporium* infection. A higher score indicates a higher resistance. Data are collected only when sufficient selection pressure exists in the experiment measured.

HD SMT=HEAD SMUT (*Sphacelotheca reiliana*): This indicates the percentage of plants not infected. Data are collected only when sufficient selection pressure exists in the experiment measured.

HSKCVR=HUSK COVER: A 1 to 9 score based on performance relative to key checks, with a score of 1 indicating very short husks, tip of ear and kernels showing;

5 is intermediate coverage of the ear under most conditions, sometimes with thin husk; and a 9 has husks extending and closed beyond the tip of the ear. Scoring can best be done near physiological maturity stage or any time during dry down until harvested.

HTFRM=Near-infrared transmission spectroscopy, NIT, prediction of fermentables.

HYBRID VARIETY: A substantially heterozygous hybrid line and minor genetic modifications thereof that retain the overall genetics of the hybrid line.

INBRED: A variety developed through inbreeding or doubled haploidy that preferably comprises homozygous alleles at about 95% or more of its loci. An inbred can be reproduced by selfing or growing in isolation so that the plants can only pollinate with the same inbred variety.

INTROGRESS ION: The process of transferring genetic material from one genotype to another.

KERNEL PERICARP COLOR is scored when kernels have dried down and is taken at or about 65 days after 50% silk. Score codes are: Colorless=1; Red with white crown=2; Tan=3; Bronze=4; Brown=5; Light red=6; Cherry red=7.

KER_WT=KERNEL NUMBER PER UNIT WEIGHT (Pounds or Grams): The number of kernels in a specific measured weight; determined after removal of extremely small and large kernels.

LINKAGE: Refers to a phenomenon wherein alleles on the same chromosome tend to segregate together more often than expected by chance if their transmission was independent.

LINKAGE DISEQUILIBRIUM: Refers to a phenomenon wherein alleles tend to remain together in linkage groups when segregating from parents to offspring, with a greater frequency than expected from their individual frequencies.

LOCUS: A specific location on a chromosome.

LOCUS CONVERSION: (Also called TRAIT CONVERSION) A locus conversion refers to plants within a variety that have been modified in a manner that retains the overall genetics of the variety and further comprises one or more loci with a specific desired trait, such as male sterility, insect resistance, disease resistance or herbicide tolerance or resistance. Examples of single locus conversions include mutant genes, transgenes and native traits finely mapped to a single locus. One or more locus conversion traits may be introduced into a single corn variety.

LRTLPN=LATE ROOT LODGING: An estimate of the percentage of plants that do not root lodge after anthesis through harvest; plants that lean from the vertical axis at an approximately 30-degree angle or greater would be considered as root lodged. Data are collected only when sufficient selection pressure exists in the experiment measured.

LRTLSC=LATE ROOT LODGING SCORE: Score for severity of plants that lean from a vertical axis at an approximate 30-degree angle or greater which typically results from strong winds after flowering. Recorded prior to harvest when a root-lodging event has occurred. This lodging results in plants that are leaned or "lodged" over at the base of the plant and do not straighten or "goose-neck" back to a vertical position. Expressed as a 1 to 9 score with 9 being no lodging. Data are collected only when sufficient selection pressure exists in the experiment measured.

MALE STERILITY: A male sterile plant is one which produces no viable pollen no (pollen that is able to fertilize the egg to produce a viable seed). Male sterility prevents self pollination. These male sterile plants are therefore useful in hybrid plant production.

MDMCPX=MAIZE DWARF MOSAIC COMPLEX (MDMV=Maize Dwarf Mosaic Virus and MCDV=Maize Chlorotic Dwarf Virus). A 1 to 9 visual rating indicating the resistance to Maize Dwarf Mosaic Complex. A higher score indicates a higher resistance. Data are collected only when sufficient selection pressure exists in the experiment measured.

MILKLN=percent milk in mature grain.

MST=HARVEST MOISTURE: The moisture is the actual percentage moisture of the grain at harvest.

NEI DISTANCE: A quantitative measure of percent similarity between two varieties. Nei's distance between varieties A and B can be defined as 1−(2*number alleles in common/(number alleles in A+number alleles in B). For example, if varieties A and B are the same for 95 out of 100 alleles, the Nei distance would be 0.05. If varieties A and B are the same for 98 out of 100 alleles, the Nei distance would be 0.02. Free software for calculating Nei distance is available on the internet at multiple locations. See Nei, Proc Natl Acad Sci, 76:5269-5273 (1979).

NLFBLT=NORTHERN LEAF BLIGHT (*Helminthosporium turcicum* or *Exserohilum turcicum*): A 1 to 9 visual rating indicating the resistance to Northern Leaf Blight. A higher score indicates a higher resistance. Data are collected only when sufficient selection pressure exists in the experiment measured.

NUCLEIC ACID: An acidic, chainlike biological macromolecule consisting of multiple repeat units of phosphoric acid, sugar, and purine and pyrimidine bases.

OILT=GRAIN OIL: Absolute value of oil content of the kernel as predicted by Near-Infrared Transmittance and expressed as a percent of dry matter.

PERCENT IDENTITY: Percent identity as used herein refers to the comparison of the alleles present in two varieties. For example, when comparing two inbred plants to each other, each inbred plant will have the same allele (and therefore be homozygous) at almost all of their loci. Percent identity is determined by comparing a statistically significant number of the homozygous alleles of two varieties. For example, a percent identity of 90% between X95R013 and other variety means that the two varieties have the same homozygous alleles at 90% of their loci.

PLANT: As used herein, the term "plant" includes reference to an immature or mature whole plant, including a plant that has been detasseled or from which seed or grain has been removed. Seed or embryo that will produce the plant is also considered to be the plant.

PLANT PART: As used herein, the term "plant part" includes leaves, stems, roots, seed, grain, embryo, pollen, ovules, flowers, ears, cobs, husks, stalks, root tips, anthers, pericarp, silk, tissue, cells and the like. In some embodiments, the plant part contains at least one cell of hybrid maize variety X95R013 or a locus conversion thereof.

PLATFORM indicates the variety with the base genetics and the variety with the base genetics comprising locus conversion(s). There can be a platform for the inbred maize variety and the hybrid maize variety.

PLTHT=PLANT HEIGHT: This is a measure of the height of the plant from the ground to the tip of the tassel in inches.

POLSC=POLLEN SCORE: A 0 to 9 visual rating indicating the amount of pollen shed. The higher the score the more pollen shed.

POLWT=POLLEN WEIGHT: This is calculated by dry weight of tassels collected as shedding commences minus dry weight from similar tassels harvested after shedding is complete.

RM=RELATIVE MATURITY: This is a predicted relative maturity based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

PROT=GRAIN PROTEIN: Absolute value of protein content of the kernel as predicted by Near-Infrared Transmittance and expressed as a percent of dry matter.

RESISTANCE: Synonymous with tolerance. The ability of a plant to withstand exposure to an insect, disease, herbicide or other condition. A resistant plant variety will have a level of resistance higher than a comparable wild-type variety.

ROOT LODGING: Root lodging is the percentage of plants that do not root lodge; plants that lean from the vertical axis at an approximately 30-degree angle or greater would be counted as root lodged. Data are collected only when sufficient selection pressure exists in the experiment measured.

SEED: Fertilized and ripened ovule, consisting of the plant embryo, varying amounts of stored food material, and a protective outer seed coat. Synonymous with grain.

SEL IND=SELECTION INDEX: The selection index gives a single measure of the hybrid's worth based on information for multiple traits. A maize breeder may utilize his or her own set of traits for the selection index. One of the traits that is almost always included is yield. The selection index data presented in the tables represent the mean value averaged across testing stations.

SELF POLLINATION: A plant is self-pollinated if pollen from one flower is transferred to the same or another flower of the same plant.

SIB POLLINATION: A plant is sib-pollinated when individuals within the same family or variety are used for pollination.

SITE SPECIFIC INTEGRATION: Genes that create a site for site specific DNA integration. This includes the introduction of FRT sites that may be used in the FLP/FRT system and/or Lox sites that may be used in the Cre/Loxp system. For example, see WO 99/25821.

SLFBLT=SOUTHERN LEAF BLIGHT (*Helminthosporium maydis* or *Bipolaris maydis*): A 1 to 9 visual rating indicating the resistance to Southern Leaf Blight. A higher score indicates a higher resistance. Data are collected only when sufficient selection pressure exists in the experiment measured.

SNP=SINGLE-NUCLEOTIDE POLYMORPHISM: is a DNA sequence variation occurring when a single nucleotide in the genome differs between individual plant or plant varieties. The differences can be equated with different alleles, and indicate polymorphisms. A number of SNP markers can be used to determine a molecular profile of an individual plant or plant variety and can be used to compare similarities and differences among plants and plant varieties.

SOURST=SOUTHERN RUST (*Puccinia polysora*): A 1 to 9 visual rating indicating the resistance to Southern Rust. A higher score indicates a higher resistance. Data are collected only when sufficient selection pressure exists in the experiment measured.

SPKDSC=SPIKELET DENSITY SCORE: The visual 1-9 rating of how dense spikelets are on the middle tassel branches. A higher score indicates higher spikelet density.

STAGRN=STAY GREEN: Stay green is the measure of plant health near the time of black layer formation (physiological maturity). A high score indicates better late-season plant health.

STKLDS=STALK LODGING SCORE: A plant is considered as stalk lodged if the stalk is broken or crimped between the ear and the ground. This can be caused by any or a combination of the following: strong winds late in the season, disease pressure within the stalks, ECB damage or genetically weak stalks. This trait should be taken just prior to or at harvest. Expressed on a 1 to 9 scale with 9 being no lodging. Data are collected only when sufficient selection pressure exists in the experiment measured.

STLLPN=LATE STALK LODGING: This is the percent of plants that did not stalk lodge (stalk breakage or crimping) at or around late season harvest (when grain moisture is below 20%) as measured by either natural lodging or pushing the stalks and determining the percentage of plants that break or crimp below the ear. Data are collected only when sufficient selection pressure exists in the experiment measured.

STLPCN=STALK LODGING REGULAR: This is an estimate of the percentage of plants that did not stalk lodge (stalk breakage) at regular harvest (when grain moisture is between about 20% and 30%) as measured by either natural lodging or pushing the stalks and determining the percentage of plants that break below the ear. Data are collected only when sufficient selection pressure exists in the experiment measured.

STWWLT=Stewart's Wilt (*Erwinia stewartii*): A 1 to 9 visual rating indicating the resistance to Stewart's Wilt. A higher score indicates a higher resistance. Data are collected only when sufficient selection pressure exists in the experiment measured.

SSRs: Genetic markers based on polymorphisms in repeated nucleotide sequences, such as microsatellites. A marker system based on SSRs can be highly informative in linkage analysis relative to other marker systems in that multiple alleles may be present.

TASBRN=TASSEL BRANCH NUMBER: The number of tassel branches, with anthers originating from the central spike.

TASSZ=TASSEL SIZE: A 1 to 9 visual rating was used to indicate the relative size of the tassel. A higher rating means a larger tassel.

TAS WT=TASSEL WEIGHT: This is the average weight of a tassel (grams) just prior to pollen shed.

TILLER=TILLERS: A count of the number of tillers per plot that could possibly shed pollen was taken. Data are given as a percentage of tillers: number of tillers per plot divided by number of plants per plot. A tiller is defined as a secondary shoot that has developed as a tassel capable of shedding pollen.

TSTWT=TEST WEIGHT (ADJUSTED): The measure of the weight of the grain in pounds for a given volume (bushel), adjusted for MST less than or equal to 22%.

TSTWTN=TEST WEIGHT (UNADJUSTED): The measure of the weight of the grain in pounds for a given volume (bushel).

VARIETY: A maize line and minor genetic modifications thereof that retain the overall genetics of the line including but not limited to a locus conversion, a mutation, or a somoclonal variant.

YIELD BU/A=YIELD (BUSHELS/ACRE): Yield of the grain at harvest by weight or volume (bushels) per unit area (acre) adjusted to 15% moisture. The yield platform BLUP is a value derived by averaging for all members of the platform weighted by the inverse of the Standard Errors.

YLDSC=YIELD SCORE: A 1 to 9 visual rating was used to give a relative rating for yield based on plot ear piles. The higher the rating the greater visual yield appearance.

YIELDS=Silage Dry Matter Yield (tons/acre @ 100% DM)

MLKYLD=Estimated pounds of milk produced per ton of dry matter fed and is based on utilizing nutrient content and fiber digestibility ADJMLK=Estimated pounds of milk produced per acre of silage dry matter based on an equation and is MLKYLD divided by YIELDS.

SLGPRM=Silage Predicted Relative Maturity

Silage Yields (Tonnage) Adjusted to 30% Dry Matter

PCTMST=Silage Harvest Moisture %

NDFDR=Silage Fiber Digestibility Based on rumen fluid NIRS calibration

NDFDC=Silage Fiber Digestibility Based on rumen fluid NIRS calibration

All tables discussed in the Detailed Description section can be found at the end of the section.

Phenotypic Characteristics of X95R013 Hybrid Maize Variety X95R013 is a single cross maize variety and can be made by crossing inbreds 1PCWH37 and PH4D4R. Locus conversions of Hybrid Maize Variety X95R013 can be made by crossing inbreds 1PCWH37 and PH4D4R wherein 1PCWH37 and/or PH4D4R comprise a locus conversion(s).

The maize variety has shown uniformity and stability within the limits of environmental influence for all the traits as described in the Variety Description Information (see Table 1, found at the end of the section). The inbred parents of this maize variety have been self-pollinated and ear-rowed a sufficient number of generations with careful attention paid to uniformity of plant type to ensure the homozygosity and phenotypic stability necessary for use in commercial hybrid seed production. The variety has been increased both by hand and in isolated fields with continued observation for uniformity. No variant traits have been observed or are expected in X95R013.

Hybrid Maize Variety X95R013 can be reproduced by planting seeds of the inbred parent varieties, growing the resulting maize plants under cross pollinating conditions, and harvesting the resulting seed using techniques familiar to the agricultural arts.

Genotypic Characteristics of X95R013

In addition to phenotypic observations, a plant can also be described or identified by its genotype. The genotype of a plant can be characterized through a genetic marker profile. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

Particular markers used for these purposes may include any type of marker and marker profile which provides a means of distinguishing varieties. A genetic marker profile can be used, for example, to identify plants of the same variety or related varieties or to determine or validate a pedigree. In addition to being used for identification of maize variety X95R013 and its plant parts, the genetic marker profile is also useful in developing a locus conversion of X95R013.

Methods of isolating nucleic acids from maize plants and methods for performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

A method comprising isolating nucleic acids, such as DNA, from a plant, a plant part, plant cell or a seed of the maize plants disclosed herein is provided. The method can include mechanical, electrical and/or chemical disruption of the plant, plant part, plant cell or seed, contacting the disrupted plant, plant part, plant cell or seed with a buffer or solvent, to produce a solution or suspension comprising nucleic acids, optionally contacting the nucleic acids with a precipitating agent to precipitate the nucleic acids, optionally extracting the nucleic acids, and optionally separating the nucleic acids such as by centrifugation or by binding to beads or a column, with subsequent elution, or a combination thereof. If DNA is being isolated, an RNase can be included in one or more of the method steps. The nucleic acids isolated can comprise all or substantially all of the genomic DNA sequence, all or substantially all of the chromosomal DNA sequence or all or substantially all of the coding sequences (cDNA) of the plant, plant part, or plant cell from which they were isolated. The amount and type of nucleic acids isolated may be sufficient to permit whole genome sequencing of the plant from which they were isolated or chromosomal marker analysis of the plant from which they were isolated.

The methods can be used to produce nucleic acids from the plant, plant part, seed or cell, which nucleic acids can be, for example, analyzed to produce data. The data can be recorded. The nucleic acids from the disrupted cell, the disrupted plant, plant part, plant cell or seed or the nucleic acids following isolation or separation can be contacted with primers and nucleotide bases, and/or a polymerase to facilitate PCR sequencing or marker analysis of the nucleic acids. In some examples, the nucleic acids produced can be sequenced or contacted with markers to produce a genetic profile, a molecular profile, a marker profile, a haplotype, or any combination thereof. In some examples, the genetic profile or nucleotide sequence is recorded on a computer readable medium. In other examples, the methods may further comprise using the nucleic acids produced from plants, plant parts, plant cells or seeds in a plant breeding program, for example in making crosses, selection and/or advancement decisions in a breeding program. Crossing includes any type of plant breeding crossing method, including but not limited to crosses to produce hybrids, outcrossing, selfing, backcrossing, locus conversion, introgression and the like. Favorable genotypes and or marker profiles, optionally associated with a trait of interest, may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes. In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis. X95R013 and its plant parts can be identified through a molecular marker profile. Such plant parts may be either diploid or haploid. The plant part includes at least one cell of the plant from which it was obtained, such as a diploid cell, a haploid cell or a somatic cell. Also provided are plants and plant parts substantially benefiting from the use of variety X95R013 in their development, such as variety X95R013 comprising a locus conversion.

Comparisons of Maize Variety Hybrid X95R013

A breeder uses various methods to help determine which plants should be selected from segregating populations and ultimately which inbred varieties will be used to develop hybrids for commercialization. In addition to knowledge of the germplasm and plant genetics, a part of the hybrid selection process is dependent on experimental design coupled with the use of statistical analysis. Experimental design and statistical analysis are used to help determine which hybrid combinations are significantly better or different for one or more traits of interest. Experimental design methods are used to assess error so that differences between two hybrid varieties can be more accurately evaluated. Statistical analysis includes the calculation of mean values, determination of the statistical significance of the sources of variation, and the calculation of the appropriate variance components. One of ordinary skill in the art of plant breeding would know how to evaluate the traits of two plant varieties to determine if there is no significant difference between the two traits expressed by those varieties. Mean trait values may be used to determine whether trait differences are significant. Trait values should preferably be measured on plants grown under the same environmental conditions, and environmental conditions should be appropriate for the traits or traits being evaluated. Sufficient selection pressure should be present for optimum measurement of traits of interest such as herbicide tolerance or herbicide, insect or disease resistance. For example, a locus conversion of X95R013 for herbicide resistance or tolerance should be compared with an isogenic counterpart in the absence of the herbicide. In addition, a locus conversion for insect or disease resistance should be compared to the isogenic counterpart, in the absence of disease pressure or insect pressure.

BLUP, Best Linear Unbiased Prediction, values can be reported for maize hybrid X95R013 and/or maize hybrid X95R013 comprising locus conversions. BLUP values can also be reported for other hybrids adapted to the same growing region as maize hybrid X95R013 with corresponding locus conversions.

Development of Maize Hybrids using X95R013

During the inbreeding process in maize, the vigor of the varieties decreases. However, vigor is restored when two different inbred varieties are crossed to produce the hybrid progeny (F1). An important consequence of the homozygosity and homogeneity of the inbred varieties is that the hybrid between a defined pair of inbreds may be reproduced indefinitely as long as the homogeneity of the inbred parents is maintained. Once the inbreds that create a superior hybrid have been identified, a continual supply of the hybrid seed can be produced using these inbred parents and the hybrid corn plants can then be generated from this hybrid seed supply.

X95R013 or its parents may also be used to produce a double cross hybrid or a three-way hybrid. A single cross hybrid is produced when two inbred varieties are crossed to produce the F1 progeny. A double cross hybrid is produced from four inbred varieties crossed in pairs (A×B and C×D) and then the two F1 hybrids are crossed again (A×B)×(C×D). A three-way cross hybrid is produced from three inbred varieties where two of the inbred varieties are crossed (A×B) and then the resulting F1 hybrid is crossed with the third inbred variety (A×B)×C. In each case, pericarp tissue from the female parent will be a part of and protect the hybrid seed.

Another form of commercial hybrid production involves the use of a mixture of male sterile hybrid seed and male pollinator seed. When planted, the resulting male sterile hybrid plants are pollinated by the pollinator plants. This method can be used to produce grain with enhanced quality grain traits, such as high oil, because desired quality grain traits expressed in the pollinator will also be expressed in the grain produced on the male sterile hybrid plant. In this method the desired quality grain trait does not have to be incorporated by lengthy procedures such as recurrent backcross selection into an inbred parent line. One use of this method is described in U.S. Pat. Nos. 5,704,160 and 5,706,603.

Molecular data from X95R013 may be used in a plant breeding process. Nucleic acids may be isolated from a seed of X95R013 or from a plant, plant part, or cell produced by growing a seed of X95R013, or from a seed of X95R013 with a locus conversion, or from a plant, plant part, or cell of X95R013 with a locus conversion. One or more polymorphisms may be isolated from the nucleic acids. A plant having one or more of the identified polymorphisms may be selected and used in a plant breeding method to produce another plant.

Introduction of a new trait or locus into Hybrid Maize Variety X95R013

Hybrid variety X95R013 represents a new base genetic line into which a new locus or trait may be introduced or introgressed. Transformation and backcrossing represent two methods that can be used to accomplish such an introgression. The term locus conversion is used to designate the product of such an introgression.

To select and develop a superior hybrid, it is necessary to identify and select genetically unique individuals that occur in a segregating population. The segregating population is the result of a combination of crossover events plus the independent assortment of specific combinations of alleles at many gene loci that results in specific and unique genotypes. Once such a variety is developed its value to society is substantial since it is important to advance the germplasm base as a whole in order to maintain or improve traits such as yield, disease resistance, pest resistance and plant performance in extreme weather conditions. Locus conversions are routinely used to add or modify one or a few traits of such a line and this further enhances its value and usefulness to society.

Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent.

Traits may be used by those of ordinary skill in the art to characterize progeny. Traits are commonly evaluated at a significance level, such as a 1%, 5% or 10% significance level, when measured in plants grown in the same environmental conditions. For example, a locus conversion of X95R013 may be characterized as having essentially the same or essentially all of the phenotypic traits or physiological and morphological traits or characteristics as X95R013. By essentially all of the phenotypic characteristics or morphological and physiological characteristics, it is meant that all of the characteristics of a plant are recovered that are otherwise present when compared in the same environment, other than an occasional variant trait that might arise during backcrossing or direct introduction of a transgene or genetic modification. The traits used for comparison may be those traits shown in Table 1 as determined at the 5% significance level when grown under the same environmental conditions. Molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants.

A backcross or locus conversion of X95R013 can be developed when DNA sequences are introduced through backcrossing, with a parent of X95R013 utilized as the recurrent parent. Naturally occurring, modified and transgenic DNA sequences may be introduced through backcrossing techniques. A backcross or locus conversion may produce a plant with a trait or locus conversion in at least one or more backcrosses, including at least 2 backcrosses, at least 3 backcrosses, at least 4 backcrosses, at least 5 backcrosses and the like. Molecular marker assisted breeding or selection may be utilized to reduce the number of backcrosses necessary to achieve the backcross conversion. For example, see Openshaw, et al., "Marker-assisted Selection in Backcross Breeding" in: Proceedings Symposium of the Analysis of Molecular Data, August 1994, Crop Science Society of America, Corvallis, Oreg., which demonstrated that a backcross locus conversion can be made in as few as two backcrosses.

The complexity of the backcross conversion method depends on the type of trait being transferred (a single gene or closely linked genes compared to unlinked genes), the level of expression of the trait, the type of inheritance (cytoplasmic or nuclear), dominant or recessive trait expression, and the types of parents included in the cross. It is understood by those of ordinary skill in the art that for single locus or gene traits that are relatively easy to classify, the backcross method is effective and relatively easy to manage.

Desired traits that may be transferred through backcross conversion include, but are not limited to, waxy starch, sterility (nuclear and cytoplasmic), fertility restoration, grain color (white), nutritional enhancements, drought tolerance, nitrogen utilization, altered fatty acid profile, increased digestibility, low phytate, industrial enhancements, disease resistance (bacterial, fungal, or viral), insect resistance, and herbicide tolerance or resistance. A locus conversion, also called a trait conversion, can be a native trait or a transgenic trait. In addition, a recombination site itself, such as an FRT site, Lox site or other site specific integration site, may be inserted by backcrossing and utilized for direct insertion of one or more genes of interest into a specific plant variety. The trait of interest is transferred from the donor parent to the recurrent parent, in this case, an inbred parent of the maize variety disclosed herein.

A single locus may contain several transgenes, such as a transgene for disease resistance that, in the same expression vector, also contains a transgene for herbicide tolerance or resistance. The gene for herbicide tolerance or resistance may be used as a selectable marker and/or as a phenotypic trait. A single locus conversion of a site specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The backcross or locus conversion may result from either the transfer of a dominant allele or a recessive allele. Selection of progeny containing the trait of interest can be accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype and/or genotype of the recurrent parent. While occasionally additional polynucleotide sequences or genes may be transferred along with the backcross conversion, the backcross conversion variety "fits into the same hybrid combination as the recurrent parent inbred variety and contributes the effect of the additional locus added through the backcross." See Poehlman et al. (1995) Breeding Field Crop, 4th Ed., Iowa State University Press, Ames, Iowa, pp. 132-155 and 321-344.

When one or more traits are introgressed into the variety a difference in quantitative agronomic traits, such as yield or dry down, between the variety and an introgressed version of the variety in some environments may occur. For example, the introgressed version, may provide a net yield increase in environments where the trait provides a benefit, such as when a variety with an introgressed trait for insect resistance is grown in an environment where insect pressure exists, or when a variety with herbicide tolerance is grown in an environment where the herbicide is used.

The modified X95R013 may be further characterized as having essentially the same phenotypic characteristics of maize variety X95R013 such as are listed in Table 1 when grown under the same or similar environmental conditions and/or may be characterized by percent identity to X95R013 as determined by molecular markers, such as SSR markers or SNP markers. Examples of percent identity determined using markers include at least 95%, 96%, 97%, 98%, 99% or 99.5%.

Traits can be used by those of ordinary skill in the art to characterize progeny. Traits are commonly evaluated at a significance level, such as a 1%, 5% or 10% significance level, when measured in plants grown in the same environmental conditions.

Male Sterility and Hybrid Seed Production

Hybrid seed production requires elimination or inactivation of pollen produced by the female inbred parent. Incomplete removal or inactivation of the pollen provides the potential for self-pollination. A reliable method of controlling male fertility in plants offers the opportunity for improved seed production. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile variety designated X95R013 may include one or more genetic factors, which result in cytoplasmic genetic and/or nuclear genetic male sterility. The male sterility may be either partial or complete male sterility.

Hybrid maize seed is often produced by a male sterility system incorporating manual or mechanical detasseling. Alternate strips of two inbred varieties of maize are planted in a field, and the pollen-bearing tassels are removed from one of the inbreds (female). Provided that there is sufficient isolation from sources of foreign maize pollen, the ears of the detasseled inbred will be fertilized only from the other inbred (male), and the resulting seed is therefore hybrid and will form hybrid plants.

Large scale commercial maize hybrid production, as it is practiced today, requires the use of some form of male sterility system which controls or inactivates male fertility. A reliable method of controlling male fertility in plants also offers the opportunity for improved plant breeding. This is especially true for development of maize hybrids, which relies upon some sort of male sterility system. There are several ways in which a maize plant can be manipulated so that is male sterile. These include use of manual or mechanical emasculation (or detasseling), cytoplasmic genetic male sterility, nuclear genetic male sterility, gametocides and the like.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system can be blended to insure that adequate pollen loads are available for fertilization when the hybrid plants are grown. CMS systems have been successfully used since the 1950's, and the male sterility trait is routinely back-crossed into inbred varieties.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describes a system of nuclear male sterility which includes: identifying a gene which is needed for male fertility; silencing this native gene which is needed for male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These, and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene needed for fertility is identified and an antisense to that gene is inserted in the plant (see Fabinjanski, et al. EPO 89/3010153.8 publication no. 329,308 and PCT application PCT/CA90/00037 published as WO 90/08828).

Another system for controlling male sterility makes use of gametocides. Gametocides are not a genetic system, but rather a topical application of chemicals. These chemicals affect cells that are needed for male fertility. The application of these chemicals affects fertility in the plants only for the growing season in which the gametocide is applied (see Carlson, Glenn R., and U.S. Pat. No. 4,936,904). Application of the gametocide, timing of the application and genotype specificity often limit the usefulness of the approach and it is not appropriate in all situations.

Transformation

Transgenes and transformation methods facilitate engineering of the genome of plants to contain and express heterologous genetic elements, such as foreign genetic elements, or additional copies of endogenous elements, or modified versions of native or endogenous genetic elements in order to alter at least one trait of a plant in a specific manner. Any sequences, such as DNA, whether from a different species or from the same species, which have been stably inserted into a genome using transformation are referred to herein collectively as "transgenes" and/or "transgenic events". Transgenes can be moved from one genome to another using breeding techniques which may include, for example, crossing, backcrossing or double haploid production. In some embodiments, a transformed variant of X95R013 may comprise at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Transformed versions of the claimed maize variety X95R013 containing and inheriting the transgene thereof are provided.

Numerous methods for plant transformation have been developed, including biological and physical plant transformation protocols. In addition, expression vectors and in vitro culture methods for plant cell or tissue transformation and regeneration of plants are available. See, for example, Qiudeng, Q. et al. (2014) Maize transformation technology development for commercial event generation, Frontiers in Plant Science 5: 379.

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1).

Plant transformation methods may involve the construction of an expression vector. Such a vector comprises a DNA sequence that contains a gene under the control of or operatively linked to a regulatory element, for example a promoter. The vector may contain one or more genes and one or more regulatory elements.

A transgenic event which has been stably engineered into the germ cell line of a particular maize plant using transformation techniques, could be moved into the germ cell line of another variety using traditional breeding techniques that are well known in the plant breeding arts. These varieties can then be crossed to generate a hybrid maize variety plant such as maize variety plant X95R013 which comprises a transgenic event. For example, a backcrossing approach is commonly used to move a transgenic event from a transformed maize plant to another variety, and the resulting progeny would then comprise the transgenic event(s). Also, if an inbred variety was used for the transformation then the transgenic plants could be crossed to a different inbred in order to produce a transgenic hybrid maize plant.

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. Nos. 6,118,055 and 6,284,953. In addition, transformability of a variety can be increased by introgressing the trait of high transformability from another variety known to have high transformability, such as Hi-II. See U.S. Patent Application Publication US 2004/0016030.

With transgenic or genetically modified plants, a foreign protein can be produced in commercial quantities. Thus, techniques for the selection and propagation of transformed plants, which are well understood in the art, yield a plurality of transgenic or genetically modified plants that are harvested in a conventional manner, and a foreign protein then can be extracted from a tissue of interest or from total biomass. Protein extraction from plant biomass can be accomplished by known methods which are discussed, for example, by Sack, M. et al., Curr. Opin. Biotech 32: 163-170 (2015).

Transgenic events can be mapped by one of ordinary skill in the art and such techniques are well known to those of ordinary skill in the art.

Plants can be genetically engineered or modified to express various phenotypes of agronomic interest. Through the transformation or modification of maize the expression of genes can be altered to enhance disease resistance, insect resistance, herbicide tolerance, agronomic traits, grain quality and other traits. Transformation can also be used to insert DNA sequences which control or help control male-sterility. DNA sequences native to maize as well as non-native DNA sequences can be transformed into maize and used to alter levels of native or non-native proteins. Various promoters, targeting sequences, enhancing sequences, and other DNA sequences can be inserted into the maize genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu or other genetic elements such as a FRT, Lox or other site specific integration site, antisense technology (see, e.g., U.S. Pat. Nos. 5,107,065; 5,453, 566; and 5,759,829); co-suppression (e.g., U.S. Pat. No. 5,034,323), virus-induced gene silencing; target-RNA-specific ribozymes; hairpin structures (WO 99/53050 and WO 98/53083); MicroRNA; ribozymes; oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes That Confer Resistance to Insects or Disease and That Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. A plant resistant to a disease is one that is more resistant to a pathogen as compared to the wild type plant.

(B) A *Bacillus thuringiensis* protein, a derivative thereof or a synthetic polypeptide modeled thereon. DNA molecules encoding delta-endotoxin genes can be purchased from American Type Culture Collection (Manassas, Va.), for example, under ATCC Accession Nos. 40098, 67136, 31995 and 31998. Other non-limiting examples of *Bacillus thuringiensis* transgenes being genetically engineered are given in the following patents and patent applications: U.S. Pat. Nos. 5,188,960; 5,689,052; 5,880,275; 5,986,177; 7,105, 332; 7,208,474; WO 91/14778; WO 99/31248; WO 01/12731; WO 99/24581; WO 97/40162 and U.S. application Ser. Nos. 10/032,717; 10/414,637; 11/018,615; 11/404, 297; 11/404,638; 11/471,878; 11/780,501; 11/780,511; 11/780,503; 11/953,648; and Ser. No. 11/957,893.

(C) An insect-specific hormone or pheromone such as an ecdysteroid and juvenile hormone, a variant thereof, a mimetic based thereon, or an antagonist or agonist thereof.

(D) An insect-specific peptide which, upon expression, disrupts the physiology of the affected pest. For example, an insect diuretic hormone receptor or an allostatin. See also U.S. Pat. No. 5,266,317 disclosing genes encoding insect-specific toxins.

(E) An enzyme responsible for a hyperaccumulation of a monoterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also U.S. Pat. Nos. 6,563,020; 7,145,060 and 7,087,810.

(G) A molecule that stimulates signal transduction. For example, calmodulin cDNA clones.

(H) A hydrophobic moment peptide. See PCT application WO 95/16776 and U.S. Pat. No. 5,580,852 disclosure of peptide derivatives of Tachyplesin which inhibit fungal plant pathogens) and PCT application WO 95/18855 and U.S. Pat. No. 5,607,914 (teaches synthetic antimicrobial peptides that confer disease resistance).

(I) A membrane permease, a channel former or a channel blocker.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance may been conferred upon transformed plants against, for example, alfalfa mosaic virus, cucumber mosaic virus, tobacco streak virus, potato virus X, potato virus Y, tobacco etch virus, tobacco rattle virus and tobacco mosaic virus.

(K) An insect-specific antibody or an immunotoxin derived therefrom. For example, an antibody targeted to a critical metabolic function in the insect gut would inactivate an affected enzyme, killing the insect.

(L) A virus-specific antibody. Plants expressing recombinant antibody genes may be protected from virus attack.

(M) A developmental-arrestive protein produced in nature by a pathogen or a parasite. For example, fungal endo alpha-1,4-D-polygalacturonases facilitate fungal colonization and plant nutrient release by solubilizing plant cell wall homo-alpha-1,4-D-galacturonase.

(N) A developmental-arrestive protein produced in nature by a plant. For example, plants expressing the barley ribosome-inactivating gene may have an increased resistance to fungal disease.

(O) Genes involved in the Systemic Acquired Resistance (SAR) Response and/or the pathogenesis related genes (P) Antifungal genes. See, e.g., U.S. application Ser. Nos. 09/950,933; 11/619,645; 11/657,710; 11/748,994; 11/774,121 and U.S. Pat. Nos. 6,891,085 and 7,306,946.

(Q) Detoxification genes, such as for fumonisin, beauvericin, moniliformin and zearalenone and their structurally related derivatives. For example, see U.S. Pat. Nos. 5,716,820; 5,792,931; 5,798,255; 5,846,812; 6,083,736; 6,538,177; 6,388,171 and 6,812,380.

(R) Cystatin and cysteine proteinase inhibitors. See U.S. Pat. No. 7,205,453.

(S) Defensin genes. See, e.g., WO03000863 and U.S. Pat. Nos. 6,911,577; 6,855,865; 6,777,592 and 7,238,781.

(T) Genes conferring resistance to nematodes. See, e.g., PCT Application WO96/30517; PCT Application WO93/19181, WO 03/033651 and U.S. Pat. Nos. 6,284,948 and 7,301,069.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes.

(V) Genes that confer resistance to Brown Stem Rot, such as described in U.S. Pat. No. 5,689,035.

(W) Genes that confer resistance to *Colletotrichum*, such as described in US Patent publication US20090035765. This includes the Rcg locus that may be utilized as a single locus conversion.

2. Transgenes That Confer Tolerance to A Herbicide, For Example:

(A) A herbicide that inhibits the growing point or meristem, such as an imidazolinone or a sulfonylurea. Exemplary genes in this category code for mutant acetolactate synthase (ALS) and acetohydroxyacid synthase (AHAS) enzyme as described, for example, in U.S. Pat. Nos. 5,605,011; 5,013,659; 5,141,870; 5,767,361; 5,731,180; 5,304,732; 4,761,373; 5,331,107; 5,928,937; and 5,378,824; US Patent Publication No. 20070214515, and international publication WO 96/33270.

(B) Glyphosate (tolerance imparted by mutant 5-enolpyruvl-3-phoshikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835, which discloses the nucleotide sequence of a form of EPSPS which can confer glyphosate tolerance. U.S. Pat. No. 5,627,061 also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582.

Glyphosate tolerance is also imparted to plants that express a gene that encodes a glyphosate oxido-reductase enzyme as described more fully in U.S. Pat. Nos. 5,776,760 and 5,463,175. In addition, glyphosate tolerance can be imparted to plants by the over expression of genes encoding glyphosate N-acetyltransferase. See, for example, US2004/0082770; US2005/0246798; and US2008/0234130. A DNA molecule encoding a mutant aroA gene can be obtained under ATCC accession No. 39256, and the nucleotide sequence of the mutant gene is disclosed in U.S. Pat. No. 4,769,061. European Patent Application No. 0 333 033 and U.S. Pat. No. 4,975,374 disclose nucleotide sequences of glutamine synthetase genes which confer tolerance to herbicides such as L-phosphinothricin. The nucleotide sequence of a phosphinothricin-acetyltransferase gene is provided in European Patent Nos. 0 242 246 and 0 242 236. See also, U.S. Pat. Nos. 5,969,213; 5,489,520; 5,550,318; 5,874,265; 5,919,675; 5,561,236; 5,648,477; 5,646,024; 6,177,616 B1; and 5,879,903. Exemplary genes conferring resistance to phenoxy propionic acids, cyclohexanediones and cyclohexones, such as sethoxydim and haloxyfop, are the Acc1-S1, Acc1-S2 and Acc1-S3 genes.

(C) A herbicide that inhibits photosynthesis, such as a triazine (psbA and gs+ genes), glutathione S-transferase and a benzonitrile (nitrilase gene) such as bromoxynil. Nucleotide sequences for nitrilase genes are disclosed in U.S. Pat. No. 4,810,648 to Stalker, and DNA molecules containing these genes are available under ATCC Accession Nos. 53435, 67441 and 67442.

(D) Other genes that confer tolerance to herbicides include: a gene encoding a chimeric protein of rat cytochrome P4507A1 and yeast NADPH-cytochrome P450 oxidoreductase, genes for glutathione reductase and superoxide dismutase, and genes for various phosphotransferases.

(E) A herbicide that inhibits protoporphyrinogen oxidase (protox or PPO) is necessary for the production of chlorophyll, which is necessary for all plant survival. The protox enzyme serves as the target for a variety of herbicidal compounds. PPO-inhibitor herbicides can inhibit growth of all the different species of plants present, causing their total destruction. The development of plants containing altered protox activity which are tolerant to these herbicides are described, for example, in U.S. Pat. Nos. 6,288,306 B1; 6,282,837 B1; and 5,767,373; and international patent publication WO 01/12825.

(F) Dicamba (3,6-dichloro-2-methoxybenzoic acid) is an organochloride derivative of benzoic acid which functions by increasing plant growth rate such that the plant dies.

3. Transgenes That Confer or Contribute to an Altered Grain Characteristic, Such as:

(A) Altered Fatty Acids, for Example, by (1) Down-regulation of stearoyl-ACP desaturase to increase stearic acid content of the plant. See, e.g., WO99/64579, (2) Elevating oleic acid via FAD-2 gene modification and/or decreasing linolenic acid via FAD-3 gene modification (se, e.g., U.S. Pat. Nos. 6,063,947; 6,323,392; 6,372,965 and WO 93/11245), (3) Altering conjugated linolenic or linoleic acid content, such as in WO 01/12800, (4) Altering LEC1, AGP, Dek1, Superalt mi1ps, various Ipa genes such as Ipat Ipa3, hpt or hggt. For example, see WO 02/42424, WO 98/22604, WO 03/011015, WO02/057439, WO03/011015, U.S. Pat. Nos. 6,423,886, 6,197,561, 6,825,397, and U.S. Application Serial Nos. US2003/0079247, US2003/0204870.

(B) Altered Phosphate Content, for Example, by the (1) Introduction of a phytase-encoding gene would enhance breakdown of phytate, adding more free phosphate to the transformed plant.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 05/113778 and/or by altering inositol kinase activity as in WO 02/059324, US2003/0009011, WO 03/027243, US2003/0079247, WO 99/05298, U.S. Pat. Nos. 6,197,561, 6,291,224, 6,391,348, WO2002/059324, US2003/0079247, Wo98/45448, WO99/55882, WO01/04147.

(C) Altered carbohydrates affected, for example, by altering a gene for an enzyme that affects the branching pattern of starch or, a gene altering thioredoxin such as NTR and/or TRX (See U.S. Pat. No. 6,531,648) and/or a gamma zein knock out or mutant such as cs27 or TUSC27 or en27 (See U.S. Pat. No. 6,858,778 and US2005/0160488, US2005/0204418). See e.g., WO 99/10498 (improved digestibility and/or starch extraction through modification of UDP-D-xylose 4-epimerase, Fragile 1 and 2, Ref1, HCHL, C4H) and U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels, and WO 03/082899 through alteration of a homogentisate geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S.:Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is needed for male fertility; silencing this native gene which is needed for male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene.

For additional examples of nuclear male and female sterility systems and genes, see also, U.S. Pat. Nos. 5,859,341; 6,297,426; 5,478,369; 5,824,524; 5,850,014; and 6,265,640.

5. Genes that create a site for site specific DNA integration. This includes the introduction of FRT sites that may be used in the FLP/FRT system and/or Lox sites that may be used in the Cre/Loxp system. For example, see WO 99/25821. Other systems that may be used include the Gin recombinase of phage Mu, the Pin recombinase of E. coli, and the R/RS system of the pSR1 plasmid.

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009; 5,965,705; 5,929,305; 5,891,859; 6,417,428; 6,664,446; 6,706,866; 6,717,034; 6,801,104; WO2000060089; WO2001026459; WO2001035725; WO2001034726; WO2001035727; WO2001036444; WO2001036597; WO2001036598; WO2002015675; WO2002017430; WO2002077185; WO2002079403; WO2003013227; WO2003013228; WO2003014327; WO2004031349; WO2004076638; WO9809521; and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. Nos. 6,177,275, 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), WO2004076638 and WO2004031349 (transcription factors).

Using X95R013 to Develop another Maize Plant

The development of maize hybrids in a maize plant breeding program requires, in general, the development of homozygous inbred lines, the crossing of these lines, and the evaluation of the crosses. Maize plant breeding programs combine the genetic backgrounds from two or more inbred varieties or various other germplasm sources into breeding populations from which new inbred varieties are developed by selfing and selection of desired phenotypes. Hybrids also can be used as a source of plant breeding material or as source populations from which to develop or derive new maize varieties. Plant breeding techniques known in the art and used in a maize plant breeding program include, but are not limited to, recurrent selection, mass selection, bulk selection, backcrossing, making double haploids, pedigree breeding, open pollination breeding, restriction fragment length polymorphism enhanced selection, genetic marker enhanced selection, and transformation. Often combinations of these techniques are used. The inbred varieties derived from hybrids can be developed using plant breeding techniques as described above. New inbreds are crossed with other inbred varieties and the hybrids from these crosses are evaluated to determine which of those have commercial potential. The oldest and most traditional method of analysis is the observation of phenotypic traits but genotypic analysis may also be used.

Methods for producing a maize plant by crossing a first parent maize plant with a second parent maize plant wherein either the first or second parent maize plant is a maize plant of the variety X95R013 are provided. The other parent may be any other maize plant, such as another inbred variety or a plant that is part of a synthetic or natural population. Any such methods using the maize variety X95R013 in crossing or breeding are provided, such as, for example: selfing, sibbing, backcrosses, mass selection, pedigree breeding, bulk selection, hybrid production, crosses to populations, and the like.

Recurrent Selection and Mass Selection

Recurrent selection is a method used in a plant breeding program to improve a population of plants. X95R013 is suitable for use in a recurrent selection program. The method entails individual plants cross pollinating with each other to form progeny. The progeny are grown and the superior progeny selected by any number of selection methods, which include individual plant, half-sib progeny, full-sib progeny, selfed progeny and toperossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred varieties to be used in hybrids or used as parents for a synthetic cultivar. A synthetic cultivar is the resultant progeny formed by the intercrossing of several selected inbreds.

X95R013 is suitable for use in mass selection. Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self-pollination, directed pollination could be used as part of the breeding program.

Production of Double Haploids

The production of double haploids from X95R013 can also be used for the development of inbreds. Double haploids are produced by the doubling of a set of chromosomes (1N) from a heterozygous plant to produce a completely homozygous individual. For example, a method is provided of obtaining a substantially homozygous X95R013 progeny plant by obtaining a seed from the cross of X95R013 and another maize plant and applying double haploid methods to the F1 seed or F1 plant or to any successive filial generation. Methods for producing plants by doubling haploid seed generated by a cross of the plants, or parts thereof, disclosed herein with a different maize plant are provided. The use of double haploids substantially decreases the number of generations required to produce an inbred with similar genetics or characteristics to X95R013. For example, see U.S. Patent Application No. 2003/0005479. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected variety (as female) with an inducer variety. Such inducer varieties for maize include Stock 6, RWS, KEMS, or KMS and ZMS, and indeterminate gametophyte (ig) mutation.

Methods for obtaining haploid plants are also disclosed in, for example, U.S. Pat. No. 5,639,951 and US Patent Application Publication No. 20020188965.

In particular, a process of making seed substantially retaining the molecular marker profile of maize variety X95R013 is provided. Obtaining a seed of hybrid maize variety X95R013 further comprising a locus conversion, wherein representative seed is produced by crossing a first plant of variety 1PCWH37 or a locus conversion thereof with a second plant of variety PH4D4R or a locus conversion thereof, and wherein representative seed of said varieties 1PCWH37 and PH4D4R have been deposited and wherein said maize variety X95R013 further comprising a locus conversion has 92%, 93%, 94%, 95%, 96%, 97%, 98% or 99% A of the same polymorphisms for molecular markers as the plant or plant part of maize variety X95R013. Sequences for the public markers can be found, for example, in the Panzea database which is available online from Panzea. The type of molecular marker used in the molecular profile can be but is not limited to Single Nucleotide Polymorphisms, SNPs. A process of making seed retaining essentially the same phenotypic, physiological, morphological or any combination thereof characteristics of maize variety X95R013 is also contemplated. Obtaining a seed of hybrid maize variety X95R013 further comprising a locus conversion, wherein representative seed is produced by crossing a first plant of variety 1PCWH37 or a locus conversion thereof with a second plant of variety PH4D4R or a locus conversion thereof, and wherein representative seed of said varieties 1PCWH37 and PH4D4R have been deposited and wherein said maize variety X95R013 further comprising a locus conversion has essentially the same morphological characteristics as maize variety X95R013 when grown in the same environmental conditions. The same environmental conditions may be, but is not limited to, a side-by-side comparison. The characteristics can be or include, for example, those listed in Table 1. The comparison can be made using any number of professionally accepted experimental designs and statistical analysis.

Use of X95R013 in Tissue Culture

Methods of tissue culturing cells of X95R013 and a tissue culture of X95R013 is provided. As used herein, the term "tissue culture" includes plant protoplasts, plant cell tissue culture, cultured microspores, plant calli, plant clumps, and the like. In certain embodiments, the tissue culture comprises embryos, protoplasts, meristematic cells, pollen, leaves or anthers derived from immature tissues of pollen, flowers, kernels, ears, cobs, leaves, husks, stalks, roots, root tips, anthers, silk, and the like. As used herein, phrases such as "growing the seed" or "grown from the seed" include embryo rescue, isolation of cells from seed for use in tissue culture, as well as traditional growing methods.

Means for preparing and maintaining plant tissue cultures are well known in the art. See, e.g., U.S. Pat. Nos. 5,538,880; 5,550,318, and 6,437,224, the latter describing tissue issue culture of maize, including tassel/anther culture. Thus, in certain embodiments, cells are provided which upon growth and differentiation produce maize plants having the genotype and/or phenotypic characteristics of variety X95R013.

Seed Treatments and Cleaning

Methods of harvesting the grain of the F1 plant of variety X95R013 and using the F2 grain as seed for planting are provided. Also provided are methods of using the seed of variety X95R013, or selfed grain harvested from variety X95R013, as seed for planting. Embodiments include cleaning the seed, treating the seed, and/or conditioning the seed and seed produced by such cleaning, conditioning, treating or any combination thereof. Cleaning the seed is understood in the art to include removal of one or more of foreign debris such as weed seed, chaff, and non-seed plant matter from the seed. Conditioning the seed is understood in the art to include controlling the temperature and rate of dry down of the seed and storing the seed in a controlled temperature environment. Seed treatment is the application of a composition to the seed such as a coating or powder. Methods for producing a treated seed include the step of applying a composition to the seed or seed surface. Seeds are provided which have on the surface a composition. Biological active components such as bacteria can also be used as a seed treatment. Some examples of compositions include active components such as insecticides, fungicides, pesticides, antimicrobials, germination inhibitors, germination promoters, cytokinins, and nutrients. Biological active components, such as bacteria, can also be used as a seed treatment. Carriers such as polymers can be used to increase binding of the active component to the seed.

To protect and to enhance yield production and trait technologies, seed treatment options can provide additional crop plan flexibility and cost effective control against insects, weeds and diseases, thereby further enhancing the invention described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis*), *Bradyrhizobium* spp. (including one or more of *betae, canariense, elkanii, iriomotense, japonicum,* liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

INDUSTRIAL APPLICABILITY

Another embodiment is a method of harvesting the grain or plant material of the F1 plant of variety X95R013 and using the grain or plant material in a commodity. Methods of producing a commodity plant product are also provided. Examples of maize grain or plant material as a commodity plant product include, but are not limited to, oils, meals, flour, starches, syrups, proteins, cellulose, silage, and sugars. Maize grain is used as human food, livestock feed, and as raw material in industry. The food uses of maize, in addition to human consumption of maize kernels, include both products of dry-and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries. Processing the grain can include one or more of cleaning to remove foreign material and debris from the grain, conditioning, such as addition of moisture to the grain, steeping the grain, wet milling, dry milling and sifting.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of the maize variety, the plant produced from the seed, a plant produced from crossing of maize variety X95R013 and various parts of the maize plant and transgenic versions of the foregoing, can be utilized for human food, livestock feed, and as a raw material in industry.

All publications, patents, and patent applications mentioned in the specification are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

As used herein, the terms "comprises," "comprising," "includes," "including," "has," "having," "contains", "containing," "characterized by" or any other variation thereof, are intended to cover a non-exclusive inclusion.

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

Deposits

Applicant has made a deposit of at least 625 seeds of parental maize inbred varieties 1PCWH37 and PH4D4R with the Provasoli-Guillard National Center for Marine Algae and Microbiota (NCMA), 60 Bigelow Drive, East Boothbay, Me. 04544, USA, with NCMA Deposit Nos. 202301019 and 202301016, respectively. The seeds deposited with the NCMA on Jan. 18, 2023 for 202301019 and on Jan. 18, 2023 for 202301016, were obtained from the seed of the variety maintained by Pioneer Hi-Bred International, Inc., 7250 NW $62^{nd}$ Avenue, Johnston, Iowa 50131-1000 since prior to the filing date of this application. Access to this seed will be available during the pendency of the application to the Commissioner of Patents and Trademarks and persons determined by the Commissioner to be entitled thereto upon request. Upon issuance of any claims in the application, the Applicant will make available to the public, pursuant to 37 C.F.R. § 1.808, a sample(s) of the deposit of at least 625 seeds of parental maize inbred varieties 1PCWH37 and PH4D4R with the NCMA. The deposits of the seed of parental maize inbred varieties for Hybrid Maize Variety X95R013 will be maintained in the NCMA depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of the rights granted under this patent or rights applicable to Hybrid Maize Variety X95R013 and/or its parental maize inbred varieties 1PCWH37 and PH4D4R under either the patent laws or the Plant Variety Protection Act (7 USC 2321 et seq.). Unauthorized seed multiplication is prohibited.

TABLE 1

VARIETY DESCRIPTION INFORMATION-* X95R013

| | | | | |
|---|---|---|---|---|
| 1. | TYPE & YIELD: | | | |
| | Grain Texture | DENT | | |
| | Yield (bushels per acre) | 221 | | |
| | Yield (Tonnage per acre @ 0% dry matter) | 8.4 | | |
| | | Days | Heat Units | |
| 2. | MATURITY: | | | |
| | Comparative Relative Maturity (CRM) | 97 | | |
| | Planting to 50% of plants in silk | 50 | 1220 | |
| | | Value | SE | Number |
| 3. | PLANT: | | | |
| | Plant Height (to flag leaf) (cm) | 258.4 | | ~15 |
| | Ear Height (to base of top ear node) (cm) | 107.6 | 9.8 | 13 |
| | Length of Top Ear Internode (cm) | 19.4 | 1.5 | 5 |
| | Number of Nodes Above Ground | 14 | 0.63 | 5 |
| | Anthocyanin of Brace Roots: | 2 | | |
| | 1 = absent, 2 = faint, 3 = moderate, 4 = dark | | | |
| 4. | LEAF: | | | |
| | Width of Ear Node Leaf (cm) | 9 | 0.63 | 5 |
| | Length of Ear Node Leaf (cm) | 95.2 | 3.97 | 5 |
| | Number of Leaves Above Top Ear | 6.4 | 0.49 | 5 |
| | Leaf Angle (Degrees) | 30 | 7.07 | 5 |
| | (at anthesis, 2nd leaf above top ear to the stalk) | | | |
| | Leaf Color | V. Dark Green | | |
| | Brown Mid Rib (BMR) | No | | |
| | Leaf Attitude | Semi-erect | | |
| | (appearance of leaf above top ear) | | | |
| | Leaf Sheath Pubescence: | 7 | | |
| | 1 = none to 9 = peach-like fuzz | | | |
| 5. | TASSEL: | | | |
| | Number of Primary Lateral Branches | 5.2 | 0.98 | 5 |
| | Number of Secondary Branches | 0 | 0 | 5 |
| | Branch Angle from Central Spike (Degrees) | 30 | 10.95 | 5 |
| | Tassel Length: | 59.2 | 5.71 | 5 |
| | (from peduncle node to tassel tip) (cm) | | | |
| | Peduncle Length: | 21.6 | 4.96 | 5 |
| | (From top leaf node to lower branch) (cm) | | | |
| | Central Spike Length (cm) | 29 | 2.28 | 5 |
| | Flag Leaf Length (cm) | 43.8 | 1.17 | 5 |
| | (from flag leaf collar to tassel tip) | | | |
| | Pollen Shed: 0 = male sterile, 9 = heavy shed | 6 | | |
| | Anther Color: | Light Red | | |
| | Glume Color: | | | |
| 6a. | EAR (Unhusked ear): | | | |
| | Silk color: (~3 days after silk emergence) | Green-Yellow | | |
| | Dry husk color: (~65 days after 50% silking) | White | | |
| | Husk Tightness:(1 = very loose, 9 = very tight) | 7 | | |
| | Husk Extension (at harvest): | | | |
| | 1 = short (ears exposed), 2 = medium (<8 cm), | | | |
| | 3 = long (8-10 cm), 4 = very long (>10 cm) | | | |
| | Ear Position at Maturity | 1 | | |
| 6b. | EAR (Husked ear data): | | | |
| | Length of Interior Husk (cm) | 19.1 | 2.06 | 5 |
| | Shank Length (cm) | 8.3 | 2.63 | 4 |
| | Ear Length (cm) | 14.5 | 2.85 | 5 |
| | Ear Diameter at mid-point (mm) | 47.8 | 0.25 | 5 |
| | Ear Weight (gm) | 152.5 | 46.4 | 5 |
| | Number of Kernel Rows | 16.3 | 1.09 | 5 |
| | Number of Kernels Per Row | 28 | 7.37 | 5 |
| | Kernel Rows: 1 = indistinct, 2 = distinct | 2 | | |
| | Row Alignment: | 1 | | |
| | 1 = straight, 2 = slightly curved, 3 = spiral | | | |

TABLE 1-continued

| | VARIETY DESCRIPTION INFORMATION-* X95R013 | | | |
|---|---|---|---|---|
| | Ear Taper: | 2 | | |
| | 1 = slight cylind., 2 = average, 3 = extreme conic. | | | |
| 7. | KERNEL (Dried): | | | |
| | Kernel Length (mm) | 12.7 | 1.51 | 38 |
| | Kernel Width (mm) | 7.9 | 0.77 | 38 |
| | Kernel Thickness (mm) | | | |
| | Kernel Pericarp color | | Clear | |
| | Aleurone Color Pattern | 1 | | |
| | Aleurone Color | | Yellow | |
| | Hard Endosperm Color | | Yellow | |
| 8. | COB:ValueSE Number | | | |
| | Cob Diameter at mid-point (mm) | 28.5 | 0.13 | 5 |
| | Cob ColorPink-Orange | | | |

*Wherein X95R013 has one or more locus conversion(s) for insect control and/or herbicide tolerance.
Number is the number of individual plants that were scored.
Value is an average if more than one plant or plot is scored.

What is claimed is:

1. A seed of hybrid maize variety X95R013, representative seed produced by crossing a first plant of variety 1PCWH37 with a second plant of variety PH4D4R, wherein representative seed of the varieties 1PCWH37 and PH4D4R have been deposited under NCMA Accession Numbers 202301019 and 202301016, respectively.

2. A plant or plant part of hybrid maize variety X95R013 grown from the seed of claim 1, wherein the plant part comprises at least one cell of hybrid maize variety X95R013.

3. A method of producing the seed of claim 1, the method comprising crossing a plant of variety 1PCWH37 with a plant of variety PH4D4R.

4. The seed of claim 1, further comprising a transgene, wherein the transgene is introduced by backcrossing or genetic transformation into the variety 1PCWH37, the variety PH4D4R, or both varieties 1PCWH37 and PH4D4R, and wherein the seed produces a plant having otherwise all the physiological and morphological characteristics of maize variety X95R013 when grown under the same environmental conditions.

5. A seed of hybrid maize variety X95R013 further comprising a single locus conversion, wherein a plant grown from the seed comprises a trait conferred by the single locus conversion, and wherein the seed is produced by crossing a first plant of variety 1PCWH37 with a second plant of variety PH4D4R, wherein the first plant, the second plant or both further comprise the single locus conversion, and wherein representative seed of the varieties 1PCWH37 and PH4D4R have been deposited under NCMA Accession Numbers 202301019 and 202301016, respectively, and wherein the seed produces a plant having otherwise all the physiological and morphological characteristics of maize variety X95R013 when grown under the same environmental conditions.

6. The hybrid maize variety X95R013 seed of claim 5, wherein the locus conversion confers a property selected from the group consisting of male sterility, herbicide tolerance, insect resistance, disease resistance, waxy starch, modified fatty acid metabolism, modified phytic acid metabolism, modified carbohydrate metabolism and modified protein metabolism.

7. The hybrid maize variety X95R013 seed of claim 5, further comprising a seed treatment on the surface of the seed.

8. A method for producing nucleic acids, the method comprising isolating nucleic acids from the hybrid maize variety X95R013 seed of claim 5.

9. A plant or plant part grown from the hybrid maize variety X95R013 seed of claim 5, the plant part comprising at least one cell of hybrid maize variety X95R013 further comprising the single locus conversion.

10. A method of producing a commodity plant product comprising starch, syrup, silage, fat or protein, the method comprising producing the commodity plant product from the plant or plant part of claim 9.

11. A method for producing a second maize plant, the method comprising applying plant breeding techniques to the plant or plant part of claim 9 to produce the second maize plant.

12. A method for producing a hybrid maize variety X95R013 seed further comprising a locus conversion, the method comprising crossing a first plant of variety 1PCWH37 with a second plant of variety PH4D4R, representative seed of the varieties 1PCWH37 and PH4D4R having been deposited under NCMA Accession Numbers 202301019 and 202301016, respectively, wherein at least one of the varieties 1PCWH37 and PH4D4R further comprises the locus conversion.

13. An F1 hybrid maize variety X95R013 seed further comprising a locus conversion produced by the method of claim 12, wherein the seed produces a plant expressing the traits conferred by the locus conversion and comprising otherwise all the physiological and morphological characteristics of maize variety X95R013 when grown under the same environmental conditions.

14. The seed of claim 13, further comprising a seed treatment on the surface of the seed.

15. The seed of claim 13, wherein the locus conversion confers a property selected from the group consisting of male sterility, herbicide tolerance, insect resistance, disease resistance, waxy starch, modified fatty acid metabolism, modified phytic acid metabolism, modified carbohydrate metabolism and modified protein metabolism.

16. A method for producing nucleic acids, the method comprising isolating nucleic acids from the seed of claim 13.

17. A plant or plant part produced by growing the seed of claim 13, the plant part comprising at least one F1 hybrid maize variety X95R013 cell further comprising the locus conversion.

18. A method for producing nucleic acids, the method comprising isolating nucleic acids from the plant or plant part of claim 17.

19. A method of producing a commodity plant product comprising starch, syrup, silage, fat or protein, the method comprising producing the commodity plant product from the plant or plant part of claim 17.

20. A method for producing a second maize plant, the method comprising crossing the maize plant or plant part of claim 17 with itself or with a different maize plant.

* * * * *